United States Patent [19]

DeWoskin

[11] 4,259,065
[45] Mar. 31, 1981

[54] ORTHODONTIC TRACTION APPARATUS

[75] Inventor: Irvin S. DeWoskin, St. Louis, Mo.

[73] Assignee: Orthoband Company, Inc., Barnhart, Mo.

[21] Appl. No.: 8,432

[22] Filed: Feb. 1, 1979

[51] Int. Cl.$^3$ .............................................. A61C 3/00
[52] U.S. Cl. ...................................................... 433/5
[58] Field of Search ................. 32/14 D, 14 A; 433/5

[56] References Cited

U.S. PATENT DOCUMENTS

| 702,805 | 6/1902 | Lindas | 32/14 D |
|---|---|---|---|
| 2,959,856 | 11/1960 | Gurin | 32/14 A |
| 2,968,097 | 1/1961 | DeWoskin | 32/14 D |
| 3,203,099 | 8/1965 | Interlandi | 32 14 D/ |
| 3,210,818 | 10/1965 | Wallshein | 32/14 A |
| 3,765,093 | 10/1973 | DeWoskin | 32/14 D |
| 4,115,921 | 9/1978 | Armstrong | 32/14 D |
| 4,121,341 | 10/1978 | DeWoskin | 32/14 D |
| 4,155,161 | 5/1979 | Armstrong | 32/14 D |

Primary Examiner—Gene Mancene
Assistant Examiner—John J. Wilson
Attorney, Agent, or Firm—Senniger, Powers, Leavitt and Roedel

[57] ABSTRACT

Orthodontic apparatus for applying traction to the teeth in a patient's mouth via an orthodontic instrumentality on the teeth, comprising headgear having a pair of side members to be worn on opposite sides of the patient's head. Each side member has a tensioning assembly associated therewith for applying traction to the teeth. Each tensioning assembly develops traction upon being stretched. The forward end of each tensioning assembly is adapted to be attached to the orthodontic instrumentality and the rearward end has a fastening rod adapted to be mounted on a side member by a coupler. The coupler has an unlocked and locked configuration. When unlocked, the fastening rod can slide in the coupler relative to the side member so that a predetermined magnitude of traction force may be developed. When locked, the fastening rod is secured against sliding movement so that the traction force may be maintained.

6 Claims, 4 Drawing Figures

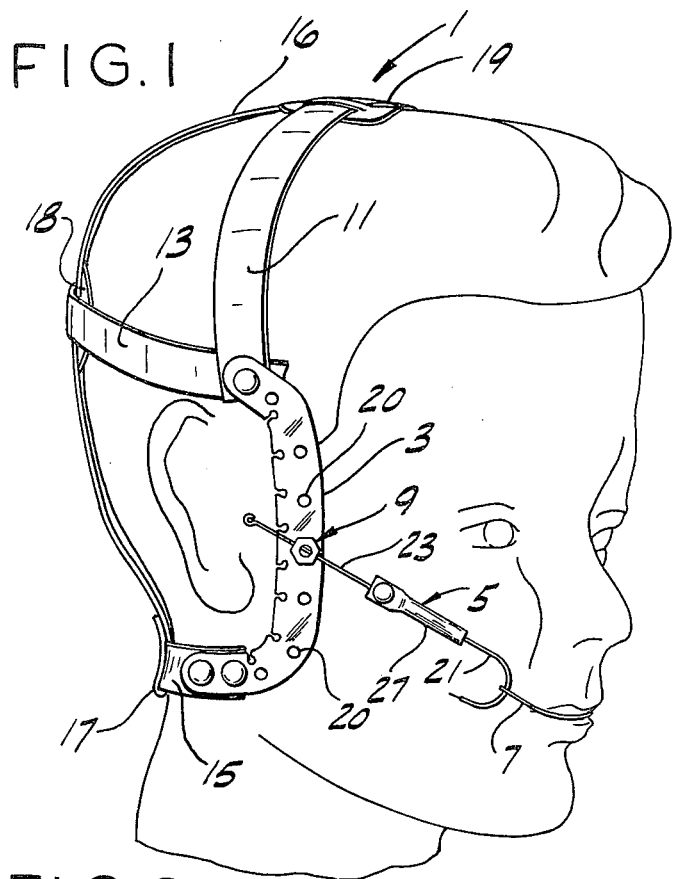
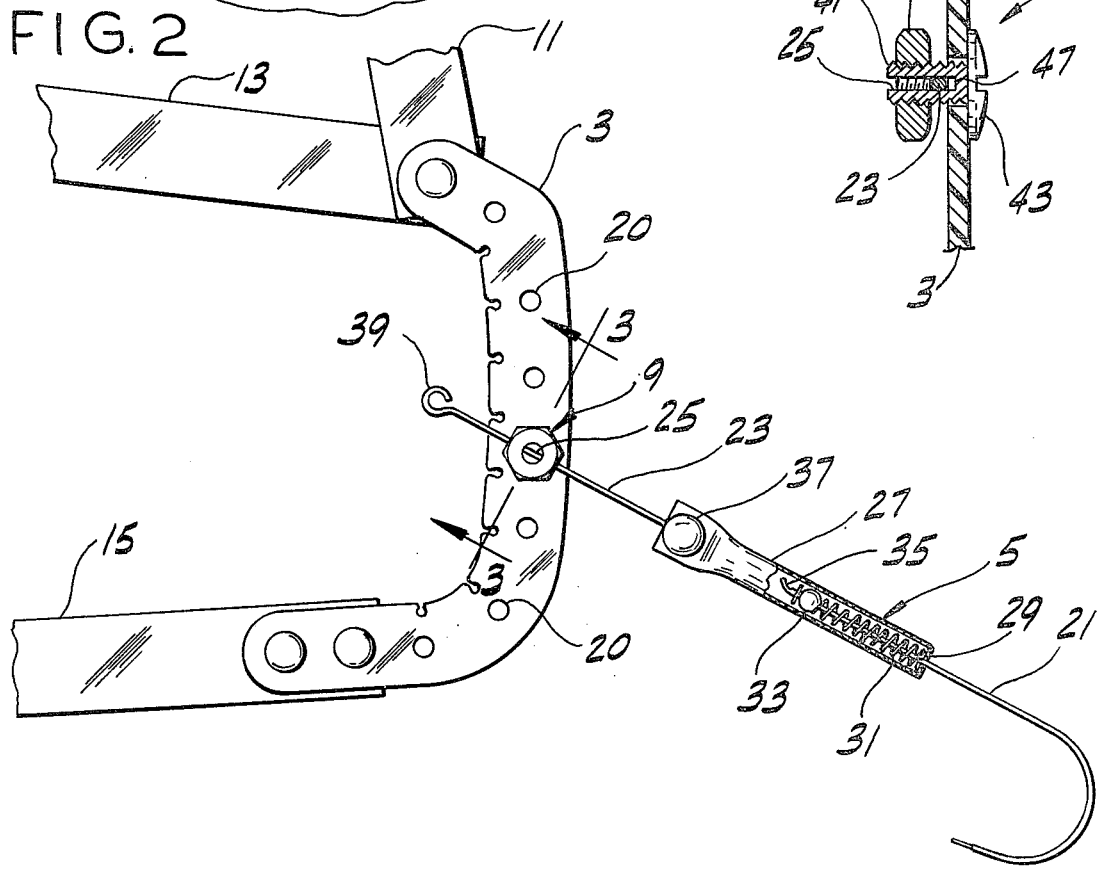
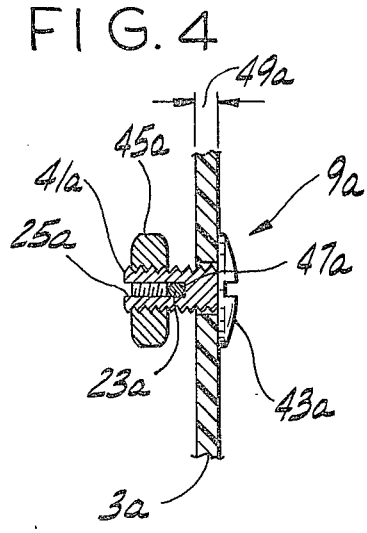
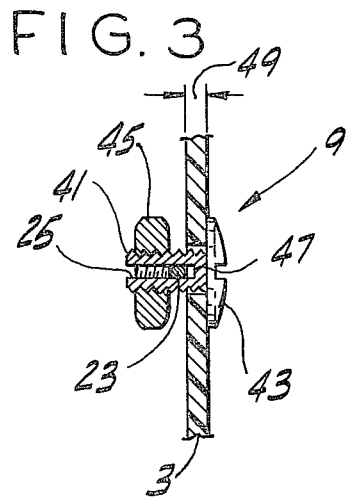

4,259,065

ORTHODONTIC TRACTION APPARATUS

BACKGROUND OF THE INVENTION

This invention relates to orthodontic apparatus, and more particularly to orthodontic apparatus capable of developing traction to be applied to the teeth in a patient's mouth via an orthodontic instrumentality on the teeth.

This invention involves an improvement in orthodontic traction apparatus of the type such as shown for example in U.S. Pat. Nos. 3,203,099, 3,765,093 and 4,121,341, generally comprising a headgear including side members adapted to be worn on opposite sides of the patient's head, a tension assembly associated with each side member for applying tension to the teeth via an orthodontic instrumentality on the teeth, when the tensioning assembly is stretched, and coupling means between the side member and the tensioning assembly.

SUMMARY OF THE INVENTION

Among the several objects of this invention may be noted the provision of improved orthodontic traction apparatus which can be readily used to develop traction force of a predetermined magnitude to be applied to the teeth in a patient's mouth via an orthodontic instrumentality on the teeth; the provision of such orthodontic apparatus which can be readily used to develop traction force along a predetermined line of action; the provision of such orthodontic apparatus which can be readily used to maintain traction force of a predetermined magnitude for extended periods of time; and the provision of such orthodontic apparatus which can be readily used to maintain the traction force along or close to a predetermined line of action for extended periods of time.

In general, apparatus of this invention comprises headgear to be worn by the patient including a pair of side members adapted to be positioned on opposite sides of the patient's head adjacent the patient's ears. Each side member has a tensioning assembly associated therewith for attachment to an orthodontic instrumentality on the teeth for applying traction to the teeth. Each tensioning assembly is adapted to develop traction upon being stretched and comprises means at one end thereof (its "forward" end) adapted to be attached to the orthodontic instrumentality and a fastening rod at its other end (its "rearward" end) adjacent the side member. A coupling means is positioned between the fastening rod of each tensioning assembly and its associated side member, the coupling means having a locked configuration and an unlocked configuration. The coupling means mounts the fastening rod on the side member for pivoting relative to the side member about an axis extending generally in side-to-side direction with respect to the patient's head and for longitudinal sliding movement of the rod in the coupling means, when the coupling means is in its unlocked configuration. The coupling means secures the fastening rod against longitudinal sliding movement of the fastening rod in the coupling means when the coupling means is in its locked configuration. With the coupling means in its unlocked configuration, traction of a predetermined magnitude may be developed by sliding the fastening rod in the coupling means. By placing the coupling means in its locked configuration, this traction force may be maintained.

Other objects and features will be in part apparent and in part pointed out hereinafter.

BRIEF DESCRIPTION OF THE DRAWINGS

FIG. 1 is a perspective of an orthodontic traction apparatus of this invention as worn on the head of a patient;

FIG. 2 is an enlarged fragment of FIG. 1;

FIG. 3 is a section of line 3—3 of FIG. 2 showing the coupling means of the FIG. 1 embodiment;

FIG. 4 is a section similar to FIG. 3 showing the coupling means of a second embodiment.

Corresponding reference characters indicate corresponding parts throughout the several views of the drawings.

DESCRIPTION OF THE PREFERRED EMBODIMENT

Referring to FIGS. 1-3 of the drawings, a first embodiment of the orthodontic traction apparatus of this invention is shown to comprise a headgear 1 including a pair of side members 3 adapted to be worn on opposite sides of the patient's head, a tensioning assembly 5 associated with each side member adapted to be attached at one end to an orthodontic instrumentality 7 on the patient's teeth and adapted to extend adjacent to the side member 3 at its other end, and coupling means 9 between each tensioning assembly 5 and its associated side member 3.

More particularly, the headgear 1 comprises an overhead strap 11 interconnecting the upper portions of the side members 3 and adapted to extend over the head of the patient. A backstrap 13 also interconnects the upper portions of the side members 3 and is adapted to extend around the back of the patient's head. A cervical strap 15 interconnects the lower portions of the side members 3 and is adapted to extend around the patient's neck. An occipital strap 16 is joined at its lower end to cervical strap 15 by loop 17, joined at an intermediate portion thereof to backstrap 13 by a back adjustment piece 18, and joined at its upper end to overhead strap 11 by a top adjustment piece 19. The occipital strap 16 is adapted to extend over the rear portion of the patient's head in a front-to-rear central vertical head plane. The side members 3 are vertically extending plates similar to those shown in U.S. Pat. Nos. 3,203,099 and 4,121,341 having a series of holes 20 of the same diameter at different elevations each adapted to receive the coupling means 9 therein.

Each tensioning assembly 5 comprises attachment means 21 at one end thereof constituting its forward end adapted to be attached to the orthodontic instrumentality 7, a fastening rod 23 at its other end constituting its rearward end adapted to extend through a recess 25 in the coupling means 9 on its respective side member 3 and an elongate tube 27 between the two ends.

The attachment means 21 extends rearwardly away from the orthodontic instrumentality 7 into the tube 27 through an opening in forward end 29 of the tube 27 and has a spring 31 and a spring abutment 33 mounted thereon (see FIG. 2). The rearward end 35 of the attachment means 21 is pinched flat so that the spring 31 and spring abutment 33 are retained on the attachment means between its rearward end 35 and the forward end 29 of the tube. The fastening rod 23 is secured to the tube 27 by a rivet 37 or other conventional fastening means so that moving the fastening rod 23 away from attachment means 21 has the effect of stretching the tensioning assembly 5 and of compressing the spring 31 to develop traction force. The position of the fastening rod 23 relative to the attachment means 21 determines the magnitude of traction force developed. An eye 39 is formed at the rearward end of the fastening rod 23. The rearward end of the tube 27 and the eye 39 prevent axial removal of the fastening rod 23 from the coupling means 9.

The coupling means 9 comprises a screw-threaded bolt 41 having a head 43 at one end thereof and means slidably receiving the respective fastening rod 21, and a nut 45 threaded on the bolt 41 at its other end. The bolt 41 is received in one of the holes 20 of the side member 3 in pivoting engagement. The means slidably receiving the respective fastening rod 21 comprises the recess 25, the recess extending across the bolt from the end of the bolt opposite its head along a central longitudinal plane of the bolt being of a width slightly greater than that of the fastening rod, and being defined, in part, by radial surface 47 at the inner end of the recess which is spaced from the inner face of the head 43 a distance less than the thickness 49 of the side member 3. The coupling means 9 has a locked and an unlocked configuration. In the unlocked configuration, the surface of the nut 45 toward the fastening rod 23 is spaced from the opposing side of the side member 3 a distance greater than the thickness of the rod 23, so that the rod 23 can slide longitudinally in the coupling means 9 between nut 45 and the side member 3. In the locked configuration, the nut 45 is rotated so that it moves toward the head 43 until the nut 45 tightly engages the rod 23 thereby securing the fastening rod between the nut 45 and the side member 3 so that longitudinal sliding movement of the fastening rod 23 in the coupling means 9 is prevented. Further, when the coupling means is in its locked configuration, pivoting of the bolt 41 relative to the side member 3 is prevented.

In use, the orthodontic traction apparatus 1 of the first embodiment is worn on the patient's head as shown in FIG. 1. The attachment means 21 of each tension assembly 5 is secured to the orthodontic instrumentality 7 in the patient's mouth. The bolt 41 of the coupling means 9 for each tension assembly 5 is placed in a predetermined hole 20 in its associated side member 3. Placement of the bolt 41 in one of the higher elevation holes 20 enables a generally upwardly and rearwardly directed traction force to be applied to the upper teeth via an orthodontic instrumentality such as a maxillary arch band, while placement in one of the lower elevation holes 20 enables a generally horizontally and rearwardly directed force to be applied to the lower teeth via an orthodontic instrumentality such as a mandibular arch band. Once each bolt 41 is in its predetermined hole 20, each fastening rod 23 is inserted into the recess 25 and the nut 45 is threaded on the bolt 41. With the coupling means in its unlocked configuration, traction force may be developed in each tensioning assembly by, for example, attaching a force applying means, such as a chain bridle and a force-indicating gauge attached to the mid-portion of the bridle (not shown), to the eye 39 on each of the rods 23 and by pulling the distant end of the force-indicating gauge away from the side members 3 in a manner similar to that shown in my U.S. Pat. No. 3,765,093. The pulling force causes the fastening rods 23 to slide within the recesses 25 and the two tension assemblies 5 to stretch so as to develop a combined traction force equal in magnitude to the pulling force. In addition, the pulling force causes the rods 23 and the bolts 41 to move into alignment with the line of action of the pulling force. Once a traction force of a predetermined magnitude and on a predetermined line of action is developed, each coupling means 9 is placed in its locked condition by rotating the nut 45 until the nut moves into tight engagement with the rod 23. The rod 23 is thus secured against longitudinal sliding movement so as to maintain the traction force at its predetermined magnitude and the coupling means is held against pivoting movement so as to maintain the rods 23 along the predetermined line of action.

Referring to FIG. 4, there is generally indicated at 9a a coupling means of a second embodiment of the orthodontic traction apparatus of this invention. The coupling means of the second embodiment is similar to that of the first embodiment except that radial surface 47a of bolt 41a is spaced from the inner surface of head 43a a distance greater than the thickness 49a of the side member 3a so that, in the locked configuration of the coupling means of the second embodiment, each fastening rod 23a is secured between the nut 45a and radial surface 47a of the bolt 41a and each bolt 41a remains free to pivot in hole 20. The second embodiment of the orthodontic traction apparatus may be used in a manner similar to that of the first embodiment to develop and to maintain traction force except that the coupling means 9a is pivotable, when in the locked configuration, to provide a limited freedom of motion of the orthodontic instrumentality 7, while maintaining the traction force along or close to its predetermined line of action. This limited freedom of motion of the orthodontic instrumentality may be preferred by orthodontists in certain cases.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Orthodontic traction apparatus for applying traction to the teeth in a patient's mouth via an orthodontic instrumentality on the teeth comprising:
   headgear including a pair of side members adapted to be worn on opposite sides of the patient's head adjacent the patient's ears;
   each side member having a tensioning assembly associated therewith for attachment to said instrumentality for applying traction to the teeth;
   each tensioning assembly being adapted to develop traction upon being stretched, and comprising means at one end thereof constituting its forward end adapted to be attached to said orthodontic instrumentality and a fastening rod at its other end constituting its rearward end adjacent said side member;
   and coupling means between the fastening rod of each tensioning assembly and its associated side member having a locked configuration and an unlocked configuration, said coupling means mounting said fastening rod on said side member for pivoting relative to said side member about an axis extending generally in side-to-side direction with respect to the patient's head and for longitudinal sliding movement of said rod in said coupling means to infinite positions within a range of adjustment when the coupling means is in its unlocked configuration, and for securing said fastening rod against longitudinal sliding movement of said rod in said coupling means when said coupling means is in its locked configuration, whereby traction of a predetermined magnitude may be developed by sliding said fastening rod in said coupling means with said coupling means in its unlocked configuration and maintained by placing said coupling means in its locked configuration, each side member having a series of holes of the same diameter at different elevations each adapted to receive said coupling means, said coupling means comprising a screw-threaded bolt having a head at one end thereof and means slidably receiving the respective fastening rod, and a nut threaded on the bolt at its other end, said bolt being received in one of said holes in pivoting engagement and extending beyond the sides of said side member, said means slidably receiving the respective fastening rod comprising a recess in the bolt extending across the bolt along a central longitudinal plane thereof, said recess being of a width slightly greater than that of the fastening rod.

2. Orthodontic traction apparatus for applying traction to the teeth in a patient's mouth via an orthodontic instrumentality on the teeth comprising:

headgear including a pair of side members adapted to be worn on opposite sides of the patient's head adjacent the patient's ears;

each side member having a tensioning assembly associated therewith for attachment to said instrumentality for applying traction to the teeth;

each tensioning assembly adapted to develop traction upon being stretched, and comprising means at one end thereof constituting its forward end adapted to be attached to said orthodontic instrumentality and a fastening rod at its other end constituting its rearward end adjacent said side member; and coupling means between the fastening rod of each tensioning assembly and its associated side member, having a locked configuration and an unlocked configuration, said coupling means mounting said fastening rod on said side member for pivoting relative to said side member about an axis extending generally in side-to-side direction with respect to the patient's head and for longitudinal sliding movement of said rod in said coupling means when the coupling means is in its unlocked configuration, and for securing said fastening rod against longitudinal sliding movement of said rod in said coupling means when said coupling means is in its locked configuration, whereby traction of a predetermined magnitude may be developed by sliding said fastening rod in said coupling means with said coupling means in its unlocked configuration and maintained by placing said coupling means in its locked configuration;

each side member having a series of holes of the same diameter at different elevations each adapted to receive said coupling means;

said coupling means comprising a screw-threaded bolt having a head at one end thereof and a nut threaded on the bolt at its other end, said bolt being received in one of said holes in pivoting engagement and extending beyond the sides of said side members, said bolt having a recess therein extending across the bolt along a central longitudinal plane of the bolt, said recess being of a width slightly greater than that of the fastening rod, said recess being defined in part of a radial surface of the bolt spaced from the inner face of the head a distance less than the thickness of said side member.

3. Apparatus as set forth in claim 2 wherein the fastening rod is received in said recess in the bolt between the nut and the side member, said nut being spaced from the side member a distance greater than the thickness of the fastening rod, when the coupling means is in its unlocked configuration, so that the nut and the side member slidingly engage the rod and said nut being moved toward the head into tight engagement with the rod, when the coupling means is in its locked configuration, so that the nut and side member secure the fastening rod to the side member.

4. Orthodontic traction apparatus for applying traction to the teeth in a patient's mouth via an orthodontic instrumentality on the teeth comprising:

headgear including a pair of side members adapted to be worn on opposite sides of the patient's head adjacent the patient's ears;

each side member having a tensioning assembly associated therewith for attachment to said instrumentality for applying traction to the teeth;

each tensioning assembly adapted to develop traction upon being stretched, and comprising means at one end thereof constituting its forward end adapted to be attached to said orthodontic instrumentality and a fastening rod at its other end constituting its rearward end adjacent said side member; and coupling means between the fastening rod of each tensioning assembly and its associated side member, having a locked configuration and an unlocked configuration, said coupling means mounting said fastening rod on said side member for pivoting relative to said side member about an axis extending generally in side-to-side direction with respect to the patient's head and for longitudinal sliding movement of said rod in said coupling means when the coupling means is in its unlocked configuration, and for securing said fastening rod against longitudinal sliding movement of said rod in said coupling means when said coupling means is in its locked configuration, whereby traction of a predetermined magnitude may be developed by sliding said fastening rod in said coupling means with said coupling means in its unlocked configuration and maintained by placing said coupling means in its locked configuration;

each side member having a series of holes of the same diameter at different elevations each adapted to receive said coupling means;

said coupling means comprising a screw-threaded bolt having a head at one end thereof and a nut threaded on the bolt at its other end, said bolt being received in one of said holes in pivoting engagement and extending beyond the sides of said side member, said bolt having a recess therein extending across the bolt along a central longitudinal plane of the bolt, said recess being of a width slightly greater than that of the fastening rod, said recess being defined, in part, by a radial surface of the bolt spaced from the inner face of the head a distance greater than the thickness of said side member.

5. Apparatus as set forth in claim 4 wherein the fastening rod is received in said recess in the bolt between the nut and said radial surface, said nut being spaced away from said radial surface a distance greater than the thickness of the fastening rod when the coupling means is in its unlocked configuration, so that the bolt and nut slidingly engage the rod and said nut is moved toward the head into tight engagement with the rod when the coupling means in in its locked configuration, so that the nut and bolt secure the fastening rod against sliding relative thereto while allowing the bolt to pivot relative to the side member.

6. Apparatus as set forth in claims 2 or 4 wherein the fastening rod has means at each end thereof for preventing axial removal of the fastening rod from the coupling means when in the unlocked configuration.

* * * * *